United States Patent
Lin

(10) Patent No.: US 9,615,978 B2
(45) Date of Patent: Apr. 11, 2017

(54) EXCREMENT SENSING DEVICE AND DIAPER WITH THE SAME

(71) Applicant: Yu-Chieh Lin, Taipei (TW)

(72) Inventor: Yu-Chieh Lin, Taipei (TW)

( * ) Notice: Subject to any disclaimer, the term of this patent is extended or adjusted under 35 U.S.C. 154(b) by 180 days.

(21) Appl. No.: 14/675,814

(22) Filed: Apr. 1, 2015

(65) Prior Publication Data

US 2015/0282993 A1  Oct. 8, 2015

(30) Foreign Application Priority Data

Apr. 2, 2014  (CN) .......................... 2014 1 0131314

(51) Int. Cl.
*A61F 13/42* (2006.01)
*G01V 8/16* (2006.01)

(52) U.S. Cl.
CPC ................ *A61F 13/42* (2013.01); *G01V 8/16* (2013.01); *A61F 2013/423* (2013.01); *A61F 2013/424* (2013.01); *A61F 2013/429* (2013.01)

(58) Field of Classification Search
CPC .......... A61F 13/00055; A61F 13/00059; A61F 13/42; A61F 2013/422; A61F 2013/423; A61F 2013/424; A61F 2013/429
See application file for complete search history.

(56) References Cited

U.S. PATENT DOCUMENTS

| | | | | |
|---|---|---|---|---|
| 6,066,774 A | * | 5/2000 | Roe | A61F 13/42 604/358 |
| 8,274,393 B2 | * | 9/2012 | Ales | A61F 13/42 340/604 |
| 2010/0305530 A1 | * | 12/2010 | Larkin | A61F 13/42 604/361 |
| 2012/0310191 A1 | * | 12/2012 | LaVon | A61F 13/505 604/361 |
| 2014/0276504 A1 | * | 9/2014 | Heil | A61F 13/42 604/361 |
| 2015/0150732 A1 | * | 6/2015 | Abir | A61F 13/42 324/658 |

\* cited by examiner

*Primary Examiner* — Lynne Anderson
(74) *Attorney, Agent, or Firm* — WPAT, PC; Justin King

(57) ABSTRACT

An excrement sensing device and a diaper with an excrement sensing device are provided. The diaper includes a detachable sensing part, an electronic part and a diaper main body. The detachable sensing part includes a first light guide structure and a second light guide structure. The electronic part includes a signal processor. A light guide gap is formed between two light guide openings of the first light guide structure and the second light guide structure. After the optical signal from the emitter is transmitted through the first light guide structure, the light guide gap and the second light guide structure, the optical signal is received by the receiver. When excrement enters the light guide gap, the optical signal is subjected to a change. In response to the change of the optical signal, the signal processor generates a warning signal.

14 Claims, 8 Drawing Sheets

EXCREMENT SENSING DEVICE AND DIAPER WITH THE SAME

FIELD OF THE INVENTION

The present invention relates to a diaper with an excrement sensing device, and more particularly to a disposable excrement sensing device capable of warning the care attendant that a diaper is dirty and a diaper with the excrement sensing device.

BACKGROUND OF THE INVENTION

People eat food every day. After digestion of food, excrements are probably discharged from the human bodies every day. However, some specific groups such as young babies, dementia patients or handicapped people often require particular cares. For preventing the excrements from overflowing everywhere, their hips are usually covered with diapers. However, the care attendant cannot directly realize whether there are excrements in the diaper. Consequently, the care attendant has to examine the use condition of the diaper on a regular time schedule, or otherwise the care attendant realizes the need of changing the diaper until the odor of excrement is smelled. Moreover, since the care attendant cannot immediately realize whether there are excrements in the diaper, the excrements have been in contact with the skin of the cared person for a certain time period before the diaper is replaced. Owing to the long-term skin contact with the excrements, the cared person who uses the diaper is readily suffered from skin problems like diaper rash.

When bacteria in urine and feces combine together, they will decompose to form irritant ammonia. This is the main cause of diaper rash. Moreover, the bacteria and acidity in feces may directly infect of the fragile skin of the infants and the elderly persons. Nowadays, the functions of the diapers in absorbing urine, keeping dry and preventing leakage are apparent and continuously improved. However, the problems of diaper rash and infections caused by the contact of skin and feces are unable to be effectively solved.

Recently, some kinds of diapers with sensing devices were introduced into the market. These sensing devices are used to sense the presence of excrements. Due to some drawbacks or limitations, these diapers are not widely used. Firstly, the cost of the diapers with sensing devices is high. As known, since the cost of the commercially-available ordinary paper diapers is relatively lower, the ordinary paper diapers are usually disposable. However, since the sensing device of the diaper is very high, the disposable deign is not cost-effective. In other words, the current diaper with the sensing device is usually not disposable. Due to the lack of the disposable feature, the original aim of the paper diaper is no longer achieved. Secondly, the safety of the diapers with the sensing devices is not satisfied. For most sensing devices, the sensors sense and transmit "electrical" signals. Since the sensing device is disposed within the diaper and close to the human body, the "electrical" signal is possibly in direct contact with the cared person because of the weight or any action of the cared person or in indirect contact with human body through the excrement medium. Even if the "electrical" signal is very low or an "insulating" means is adopted, the "electrical" signal within the diaper may result in physiological risks or psychological risks to the user. Consequently, the conventional diaper with the sensing device is not popular.

SUMMARY OF THE INVENTION

An object of the present invention provides an excrement sensing device and a diaper with an excrement sensing device in order to solve the drawbacks of the conventional technologies. The excrement sensing device comprises a detachable sensing part and an electronic part. The detachable sensing part and the electronic part are detachably combined with each other. The excrement sensing device can immediately sense the whether the excrement is discharged. The sensing element with higher cost is installed in the electronic part, wherein the electronic part can be reused. The sensing element with lower cost is installed in the detachable sensing part. The sensing element can be discarded along with the contaminated diaper main body.

In accordance with an aspect of the present invention, there is provided a diaper with an excrement sensing device. The diaper includes a detachable sensing part, an electronic part and a diaper main body. The detachable sensing part includes a first light guide structure and a second light guide structure. The first light guide structure has a first light guide opening. The second light guide structure has and a second light guide opening. A light guide gap is formed between the first light guide opening and the second light guide opening. The electronic part includes a signal processor, an emitter and a receiver. The detachable sensing part is detachably combined with the electronic part. An optical signal is emitted by the emitter. After the optical signal is transmitted through the first light guide structure, the light guide gap and the second light guide structure, the optical signal is received by the receiver. The detachable sensing part is disposed within the diaper main body. When an excrement enters the light guide gap or contacts with the detachable sensing part, the optical signal is subjected to a change. In response to the change of the optical signal, the signal processor generates a warning signal.

Preferably, the electronic part further comprises a warning device, and the warning device is in communication with the signal processor to receive the warning signal. If the warning device is a light generation device, the light generation device generates a warning light after the warning signal is sent to the light generation device. If the warning device is a sound generation device, the sound generation device generates a warning sound after the warning signal is sent to the sound generation device. If the warning device is a wireless transmitter, the wireless transmitter issues a wireless warning signal to an external electronic device after the warning signal is sent to the wireless transmitter. If the warning device comprises a light generation device and a light guide bar and the light guide bar is connected with the light generation device, plural light beams emitted by the light generation device are introduced into a front end of the light guide bar and outputted from a rear end of the light guide bar after the warning signal is received by the warning device, and the rear end of the light guide bar is exposed outside a clothing of a diaper user.

Preferably, the electronic part includes a first coupling part, and the detachable sensing part includes a second coupling part matching the first coupling part. When the first coupling part and the second coupling part are engaged with each other, the electronic part and the detachable sensing part are combined together, so that the optical signal from the emitter is introduced into the first light guide structure through an input end of the first light guide structure. After the optical signal is sequentially transmitted through the first light guide structure, the light guide gap and the second light guide structure, the optical signal is outputted from an output end of the second light guide structure and received by the receiver.

Preferably, the electronic part further includes an extension light tube structure, the first coupling part is located at an end of the extension light tube structure, and the first coupling part is engageable with the second coupling part of the detachable sensing part, wherein the extension light tube structure includes a first light channel and a second light channel, wherein when the electronic part and the detachable sensing part are combined together, the optical signal from the emitter is sequentially transmitted through the first light channel, the first light guide structure, the light guide gap, the second light guide structure and the second light channel and received by the receiver.

Preferably, the electronic part further includes a clipping part that clips the diaper main body or the clothing of the diaper user. When the diaper main body is clipped by the clipping part, the electronic part is positioned on a specified location of the diaper main body. When the clothing of the diaper user is clipped by the clipping part, the light generation device of the electronic part is exposed outside the clothing.

Preferably, the detachable sensing part further includes an adhesive, the diaper main body further includes an inner surface and an inner insert layer under the inner surface, and the inner surface of the diaper main body is made of gauze. The detachable sensing part is attached on the inner surface or the inner insert layer of the diaper main body via the adhesive, or the detachable sensing part is fixedly installed on the inner surface of the diaper main body.

Preferably, the first light guide opening of the first light guide structure is located at a rear end of the first light guide structure, and the second light guide opening of the second light guide structure is located at a rear end of the second light guide structure. The first light guide opening and the second light guide opening correspond to each other.

Preferably, the first light guide opening and the second light guide opening are aligned with each other, or at least one of the first light guide opening and the second light guide opening is equipped with a lens to concentrate the optical signal, so that the concentrated optical signal is transmitted from the first light guide structure to the second light guide structure through the light guide gap.

Preferably, at least one of the rear end of the first light guide structure and the rear end of the second light guide structure is made of a water swelling material. When the water swelling material is in contact with the excrement, the rear end formed of the water swelling material swells and occupies at least a portion of the light guide gap, so that an intensity of the optical signal passing through the light guide gap is attenuated. After the changed optical signal is received by the receiver, the warning signal is generated.

Preferably, the detachable sensing part further includes a detection test strip, and the detection test strip is arranged between the rear end of the first light guide structure and the rear end of the second light guide structure. When the detection test strip is in contact with the excrement, a color of the detection test strip is changed. After the changed optical signal is received by the receiver, the warning signal is generated.

Preferably, the detection test strip is a thin film printed with color-variable ink. When the color-variable ink is in contact with the excrement, a color of the color-variable ink becomes deeper, so that an intensity of the optical signal received by the receiver is attenuated. Alternatively, when the color-variable ink is in contact with the excrement, the color of the color-variable ink becomes lighter, so that an intensity of the optical signal received by the receiver is strengthened.

Preferably, the detachable sensing part further includes a light guide material, and the light guide material is located at the light guide gap. When the light guide material is not in contact with water, the light guide material has high transmittance. When the light guide material is in contact with water, the transmittance of the light guide material is reduced, so that an intensity of the optical signal passing through the light guide gap is attenuated. After the changed optical signal is received by the receiver, the warning signal is generated.

Preferably, the detachable sensing part further includes a light guide glue, and the light guide glue is located at the light guide gap. When the light guide glue is not in contact with water, the first light guide opening and the second light guide opening are fixed by the light guide glue, so that the first light guide opening and the second light guide opening are aligned with each other. When the light guide glue is in contact with water, the light guide glue is dissolved, cracked or disintegrated, so that the first light guide opening and the second light guide opening are no longer aligned with each other and an intensity of the optical signal passing through the light guide gap is attenuated. After the changed optical signal is received by the receiver, the warning signal is generated.

Preferably, the detachable sensing part further includes at least one supporting structure, and the at least one supporting structure is connected with the first light guide structure and the second light guide structure. The first light guide structure and the second light guide structure are separated from each other by the supporting structure, so that there is a specified distance between the first light guide opening and the second light guide opening.

Preferably, each of the first light guide structure and the second light guide structure includes at least one light guide bar or at least one optical fiber tube. The first light guide structure and the second light guide structure are arranged side by side along a horizontal direction, or the first light guide structure and the second light guide structure are arranged side by side along a vertical direction.

Preferably, the first light guide structure and the second light guide structure are arranged side by side, the first light guide opening and the second light guide opening are aligned with each other, the first light guide opening and the second light guide opening are located at first ends of the first light guide structure and the second light guide structure, and the electronic part is located at second ends of the first light guide structure and the second light guide structure.

In accordance with another aspect of the present invention, there is provided an excrement sensing device for a diaper. The excrement sensing device includes a detachable sensing part and an electronic part. The detachable sensing part includes a first light guide structure and a second light guide structure. The first light guide structure has a first light guide opening. The second light guide structure has a second light guide opening. A light guide gap is formed between the first light guide opening and the second light guide opening. The electronic part includes a signal processor, an emitter and a receiver. The detachable sensing part is detachably combined with the electronic part. An optical signal is emitted by the emitter. After the optical signal is transmitted through the first light guide structure, the light guide gap and the second light guide structure, the optical signal is received by the receiver. The detachable sensing part and the electronic part are detachably disposed on a diaper main body. When an excrement enters the light guide gap or contacts with the detachable sensing part, the optical signal is subjected to a change. In response to the change of the optical signal, the signal processor generates a warning signal.

Preferably, the electronic part further comprises a warning device, and the warning device is in communication with the signal processor to receive the warning signal. If the warning device is a light generation device, the light generation device generates a warning light after the warning signal is sent to the light generation device. If the warning device is a sound generation device, the sound generation device generates a warning sound after the warning signal is sent to the sound generation device. If the warning device is a wireless transmitter, the wireless transmitter issues a wireless warning signal to an external electronic device after the warning signal is sent to the wireless transmitter. If the warning device comprises a light generation device and a light guide bar and the light guide bar is connected with the light generation device, plural light beams emitted by the light generation device are introduced into a front end of the light guide bar and outputted from a rear end of the light guide bar after the warning signal is received by the warning device, and the rear end of the light guide bar is exposed outside a clothing of a diaper user.

Preferably, the electronic part includes a first coupling part, and the detachable sensing part includes a second coupling part matching the first coupling part. When the first coupling part and the second coupling part are engaged with each other, the electronic part and the detachable sensing part are combined together, so that the optical signal from the emitter is introduced into the first light guide structure through an input end of the first light guide structure. After the optical signal is sequentially transmitted through the first light guide structure, the light guide gap and the second light guide structure, the optical signal is outputted from an output end of the second light guide structure and received by the receiver.

Preferably, the electronic part further includes an extension light tube structure, the first coupling part is located at an end of the extension light tube structure, and the first coupling part is engageable with the second coupling part of the detachable sensing part, wherein the extension light tube structure includes a first light channel and a second light channel, wherein when the electronic part and the detachable sensing part are combined together, the optical signal from the emitter is sequentially transmitted through the first light channel, the first light guide structure, the light guide gap, the second light guide structure and the second light channel and received by the receiver.

Preferably, the electronic part further includes a clipping part that clips the diaper main body or the clothing of the diaper user. When the diaper main body is clipped by the clipping part, the electronic part is positioned on a specified location of the diaper main body. When the clothing of the diaper user is clipped by the clipping part, the light generation device of the electronic part is exposed outside the clothing.

Preferably, the detachable sensing part further includes an adhesive, the diaper main body further includes an inner surface and an inner insert layer under the inner surface, and the inner surface of the diaper main body is made of gauze. The detachable sensing part is attached on the inner surface or the inner insert layer of the diaper main body via the adhesive, or the detachable sensing part is fixedly installed on the inner surface of the diaper main body.

Preferably, the first light guide opening of the first light guide structure is located at a rear end of the first light guide structure, and the second light guide opening of the second light guide structure is located at a rear end of the second light guide structure. The first light guide opening and the second light guide opening correspond to each other.

Preferably, the first light guide opening and the second light guide opening are aligned with each other, or at least one of the first light guide opening and the second light guide opening is equipped with a lens to concentrate the optical signal, so that the concentrated optical signal is transmitted from the first light guide structure to the second light guide structure through the light guide gap.

Preferably, at least one of the rear end of the first light guide structure and the rear end of the second light guide structure is made of a water swelling material. When the water swelling material is in contact with the excrement, the rear end formed of the water swelling material swells and occupies at least a portion of the light guide gap, so that an intensity of the optical signal passing through the light guide gap is attenuated. After the changed optical signal is received by the receiver, the warning signal is generated.

Preferably, the detachable sensing part further includes a detection test strip, and the detection test strip is arranged between the rear end of the first light guide structure and the rear end of the second light guide structure. When the detection test strip is in contact with the excrement, a color of the detection test strip is changed. After the changed optical signal is received by the receiver, the warning signal is generated.

Preferably, the detection test strip is a thin film printed with color-variable ink. When the color-variable ink is in contact with the excrement, a color of the color-variable ink becomes deeper, so that an intensity of the optical signal received by the receiver is attenuated. Alternatively, when the color-variable ink is in contact with the excrement, the color of the color-variable ink becomes lighter, so that an intensity of the optical signal received by the receiver is strengthened.

Preferably, the detachable sensing part further includes a light guide material, and the light guide material is located at the light guide gap. When the light guide material is not in contact with water, the light guide material has high transmittance. When the light guide material is in contact with water, the transmittance of the light guide material is reduced, so that an intensity of the optical signal passing through the light guide gap is attenuated. After the changed optical signal is received by the receiver, the warning signal is generated.

Preferably, the detachable sensing part further includes a light guide glue, and the light guide glue is located at the light guide gap. When the light guide glue is not in contact with water, the first light guide opening and the second light guide opening are fixed by the light guide glue, so that the first light guide opening and the second light guide opening are aligned with each other. When the light guide glue is in contact with water, the light guide glue is dissolved, cracked or disintegrated, so that the first light guide opening and the second light guide opening are no longer aligned with each other and an intensity of the optical signal passing through the light guide gap is attenuated. After the changed optical signal is received by the receiver, the warning signal is generated.

Preferably, the detachable sensing part further includes at least one supporting structure, and the at least one supporting structure is connected with the first light guide structure and the second light guide structure. The first light guide structure and the second light guide structure are separated from each other by the supporting structure, so that there is a specified distance between the first light guide opening and the second light guide opening.

Preferably, each of the first light guide structure and the second light guide structure includes at least one light guide bar or at least one optical fiber tube. The first light guide structure and the second light guide structure are arranged side by side along a horizontal direction, or the first light guide structure and the second light guide structure are arranged side by side along a vertical direction.

Preferably, the first light guide structure and the second light guide structure are arranged side by side, the first light guide opening and the second light guide opening are aligned with each other, the first light guide opening and the second light guide opening are located at first ends of the first light guide structure and the second light guide structure, and the electronic part is located at second ends of the first light guide structure and the second light guide structure.

From the above descriptions, the present invention provides a diaper with an excrement sensing device. The excrement sensing device comprises a detachable sensing part and an electronic part. The detachable sensing part and the electronic part are detachably combined with each other. The electronic part comprises a signal processor with higher cost. The electronic part may be located at any position of the diaper main body with the proviso that the electronic part is not easily contaminated by the excrement. Moreover, the electronic part can be reused. Moreover, the detachable sensing part has lower cost and is discarded along with the diaper main body. The excrement sensing device of the present invention senses the excrement according to the optical signal in replace of the electrical signal. Consequently, the diaper user will not have the psychological fear of the possible electric shock. Moreover, when the excrement is discharged from the cared person, the excrement sensing device of the diaper of the present invention can immediately sense the excrement and actively notify the care attendant that it is time to replace the diaper of the cared person with a new one. By using the diaper of the present invention, the contact time of the excrement with the skin of the cared person will be largely reduced. Consequently, the use of the diaper of the present invention can effectively prevent urinary tract infection, diaper rash and other diseases. In other words, the diaper of the present invention is more user-friendly.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

Figure 1:
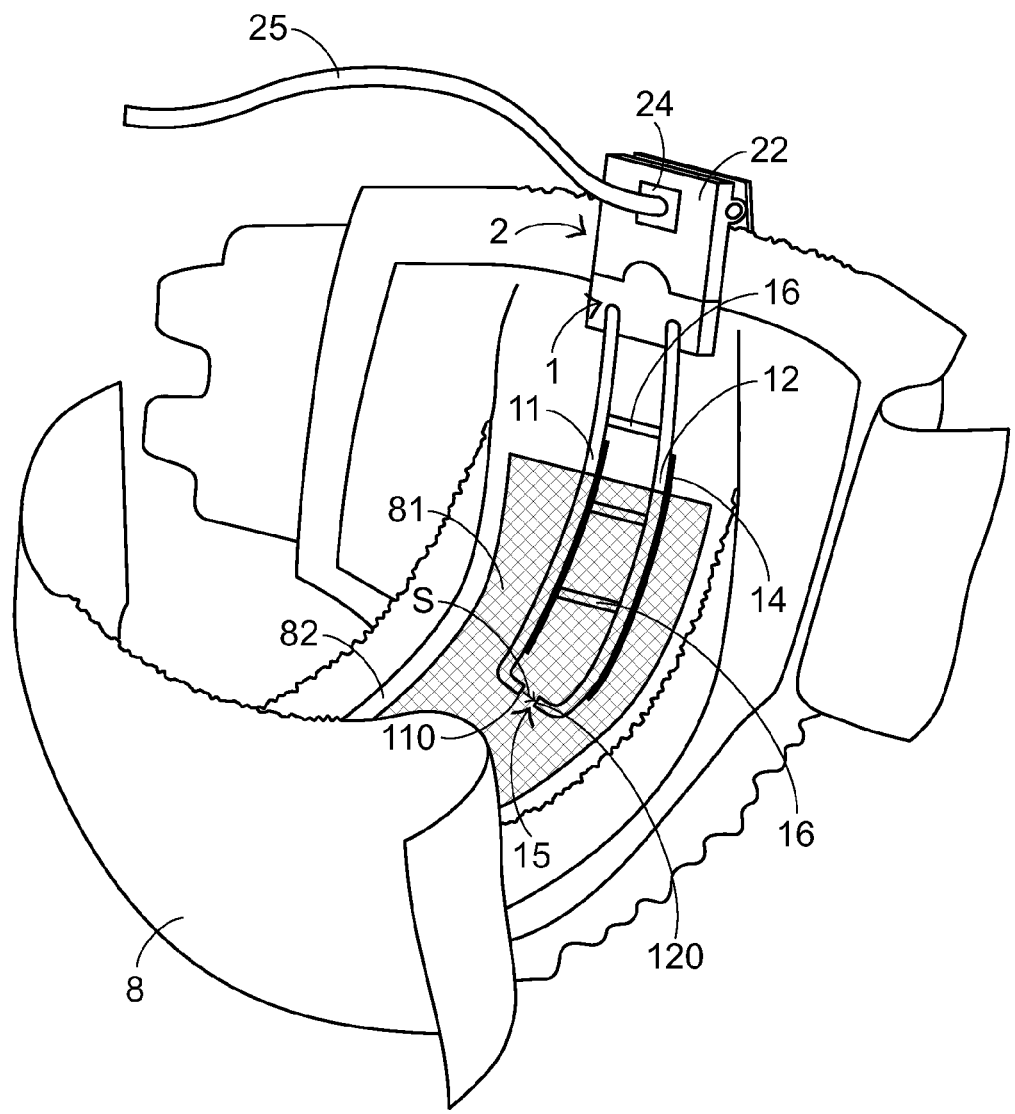
FIG. 1 is a schematic perspective view illustrating a diaper with an excrement sensing device according to an embodiment of the present invention.

The present invention will now be described more specifically with reference to the following embodiments. It is to be noted that the following descriptions of preferred embodiments of this invention are presented herein for purpose of illustration and description only. In the following embodiments and drawings, the elements irrelevant to the concepts of the present invention are omitted and not shown. For well understanding the present invention, the elements shown in the drawings are not in scale with the elements of the practical product.

Figure 2:
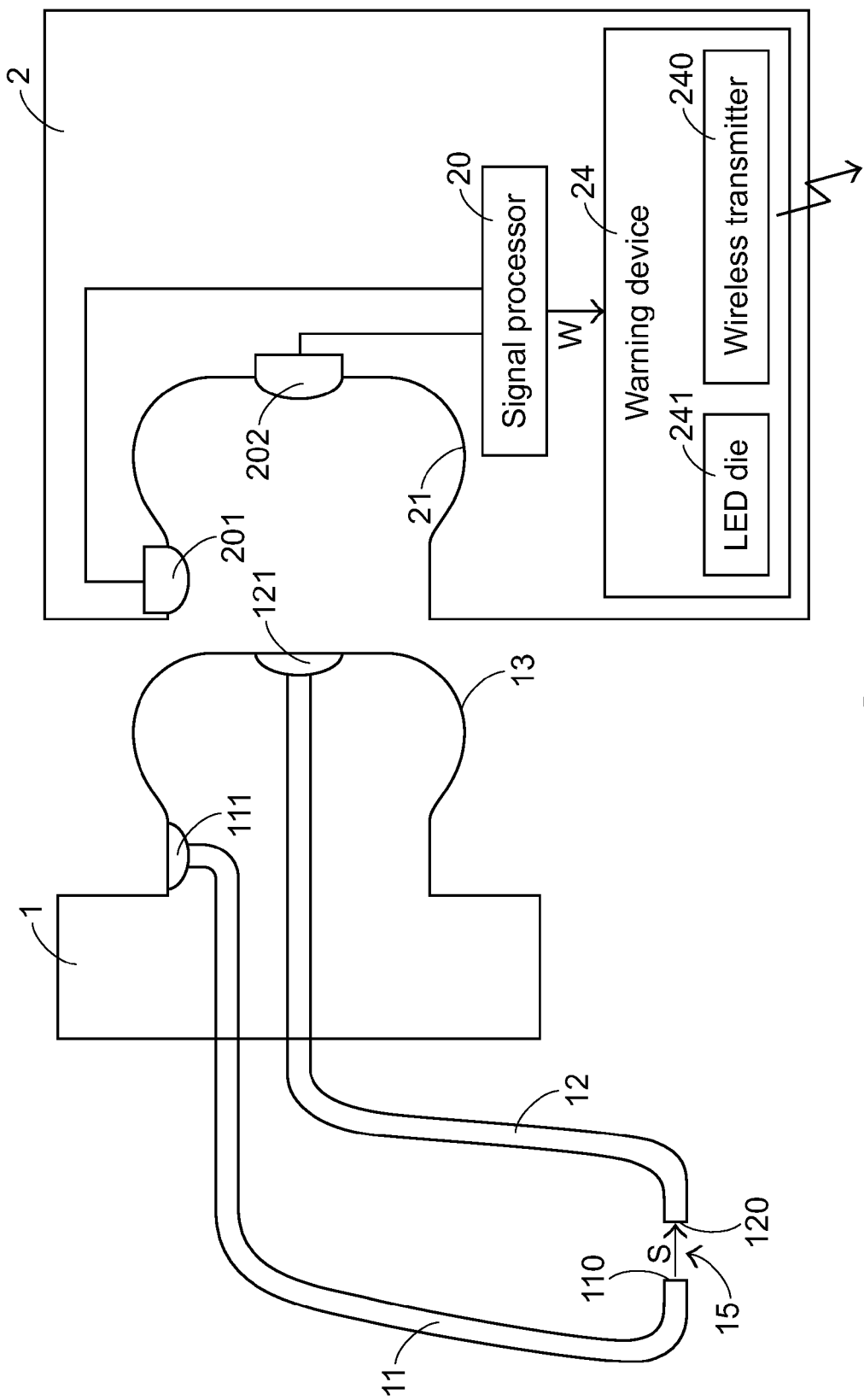
FIG. 2 schematically illustrates the relationship between an electronic part and a detachable sensing part of a diaper according to an embodiment of the present invention.

Please refer to FIGS. 1 and 2. FIG. 1 is a schematic perspective view illustrating a diaper with an excrement sensing device according to an embodiment of the present invention. FIG. 2 schematically illustrates the relationship between an electronic part and a detachable sensing part of a diaper according to an embodiment of the present invention. According to the present invention, the diaper with the sensing device comprises a detachable sensing part 1 and an electronic part 2. The detachable sensing part 1 comprises a first light guide structure 11 and a second light guide structure 12. The electronic part 2 comprises a signal processor 20. The first light guide structure 11 and the second light guide structure 12 are elongated tube structures. Moreover, the length of the first light guide structure 11 and the length of the second light guide structure 12 are substantially equal. The inner surfaces of the first light guide structure 11 and the second light guide structure 12 can guide light. An optical signal outputted from the electronic part 2 can be transmitted through the inner portions of the first light guide structure 11 and the second light guide structure 12 of the detachable sensing part 1 and returned back to the electronic part 2 so as to achieve the purpose of signal transmission.

Moreover, the first light guide structure 11 and the second light guide structure 12 have light guide openings 110 and 120, respectively. The two light guide openings 110 and 120 correspond to each other. Since the two light guide openings 110 and 120 are separated from each other by a specified distance, a light guide gap 15 is formed between the two light guide openings 110 and 120. In this embodiment, the light guide opening 110 of the first light guide structure 11 is located at a left end of the first light guide structure 11, and the light guide opening 120 of the second light guide structure 12 is located at a left end of the second light guide structure 12. Moreover, the first light guide structure 11 and the second light guide structure 12 are arranged side by side. In other words, the light guide openings 110 and 120 are both located at the same first ends of the first light guide structure 11 and the second light guide structure 12, and the electronic part 2 is located at the same second ends of the first light guide structure 11 and the second light guide structure 12. Consequently, the two light guide openings 110 and 120 are in a face-to-face arrangement so as to achieve good signal transmission efficacy. The face-to-face arrangement of the two light guide openings 110 and 120 is presented herein for purpose of illustration and description only.

The diaper of the present invention further comprises a diaper main body 8. The hip of the cared person is covered by the diaper main body 8. The sensing device is used for detecting whether excrement 9 is discharged from the cared person in time (see FIG. 9). Preferably, at least a portion of the first light guide structure 11 and at least a portion of the second light guide structure 12 are disposed on an inner surface 81 of the diaper main body 8. That is, a side of the first light guide structure 11 and a side of the second light guide structure 12 are attached on the inner surface 81 of the diaper main body 8, and another side of the first light guide structure 11 and another side of the second light guide structure 12 are contacted with the skin of the cared person. Moreover, for achieving the most precise sensing result, the light guide gap 15 is located at an optimal position near the outlets of the excretory organs of the cared person. For example, the outlets of the excretory organs include anus, urethra, or the like. Alternatively, the diaper main body 8 further comprises an inner insert layer 82 under the inner surface 81, wherein the inner insert layer 82 contains a superabsorbent polymeric material. Moreover, at least a portion of the first light guide structure 11 and at least a portion of the second light guide structure 12 are disposed within the inner insert layer 82. That is, a side of the first light guide structure 11 and a side of the second light guide structure 12 are attached on the superabsorbent polymeric material of the inner insert layer 82 of the diaper main body 8, and another side of the first light guide structure 11 and another side of the second light guide structure 12 are attached on the inner surface 81 of the diaper main body 8. Under this circumstance, the first light guide structure 11 and at least a portion of the second light guide structure 12 are not in direct with the skin of the cared person. Moreover, for achieving the most precise sensing result, the light guide gap 15 is located at the optimal position near the outlets of the excretory organs of the cared person (e.g., anus or urethra). Preferably, for providing wear comfort to the cared person, the inner surface 81 of the diaper main body 8 is made of gauze. The material of the inner surface 81 of the diaper main body 8 is presented herein for purpose of illustration and description only.

On the other hand, the detachable sensing part 1 and the electronic part 2 can be integrated as an excrement sensing device of the present invention, and the excrement sensing device can be applied to the commercially available diapers. For example, the detachable sensing part 1 and the electronic part 2 may be combined as a group and sold together. After the detachable sensing part 1 and the electronic part 2 are purchased, the combination of the detachable sensing part 1 and the electronic part 2 may be fixed on the commercially available diaper by the customer through an adhering means or a clipping means, so that the excrement sensing device is applied to the diaper. After the detachable sensing part 1 is contacted with the excrement 9, the detachable sensing part 1 will be discarded and replaced with a new one. More especially, the electronic part 2 can be reused. Alternatively, in another embodiment, the diaper is equipped with the detachable sensing part 1 when the diaper leaves the factory. That is, the detachable sensing part 1 is fixedly installed on the inner surface 81 of the diaper main body 8. As long as the electronic part 2 matching the detachable sensing part 1 is available by the consumer, the assembled excrement sensing device has the function of sensing the excrement 9.

In this embodiment, the electronic part 2 comprises an emitter 201 and a receiver 202. The first light guide structure 11 and the second light guide structure 12 are aligned and connected with the emitter 201 and the receiver 202, respectively. When the emitter 201 emits an optical signal S, the optical signal S is just transmitted through the first light guide structure 11, the light guide gap 15 and the second light guide structure 12 sequentially. Then, the optical signal S is received by the receiver 202. Since portions of the first light guide structure 11 and the second light guide structure 12 of the excrement sensing device are disposed within the diaper main body 8, the excrement 9 discharged from the cared person can easily enter the light guide gap 15 between the first light guide structure 11 and the second light guide structure 12. Under this circumstance, since the optical path of the optical signal S is disturbed, the optical signal S is subjected to a change. After the changed optical signal S is received by the signal processor 20, a warning signal W is issued to a warning device 24. Consequently, the warning device 24 generates a sound effect or a light beam to warn the care attendant of replacing the diaper of the cared person. There are some situations that the optical path of the optical signal S is disturbed by the excrement 9 and the optical signal S is subjected to the change. These situations will be illustrated later.

Hereinafter, some examples of the warning device 24 will be illustrated in more details. The warning device 24 is in communication with the signal processor 20 for receiving the warning signal W.

The warning device 24 comprises a wireless transmitter 240. After the warning signal W is sent to the wireless transmitter 240, a wireless warning signal is transmitted from the wireless transmitter 240 to an external electronic device (not shown). For example, the electronic device is a smart phone or a computer of the care attendant, or a service system of a maintenance service center, or any other surveillance or monitoring device. In response to the wireless warning signal, the external electronic device generates an image or a sound effect to warn the care attendant that it is time to replace the diaper of the cared person.

In an embodiment, the warning device 24 is a light generation device. The light generation device comprises at least one LED die 241. After the warning signal W is sent to the light generation device, the LED die 241 of the light generation device generates a warning light. When the warning light is seen by the care attendant, the care attendant realizes that it is time to replace the diaper of the cared person. Of course, the warning device may be a sound generation device in replace of the above light generation device.

Moreover, the light generation device further comprises a light guide bar 25. The light guide bar 25 is a thin, long and flexible optical fiber or other light guide tube. A front end of the light guide bar 25 is connected with the light-emitting site of the LED die 241. A rear end of the light guide bar 25 is exposed outside the clothing of the cared person. The LED die 241 generates plural light beams. The plural light beams are introduced into one end of the light guide bar 25 and outputted from the other end of the light guide bar 25. Consequently, the light beams from the LED die 241 can be outputted to the surroundings through the light guide bar 25. Moreover, since the light guide bar 25 is made of a soft material and has a sufficient length (e.g. 1 meter or longer), even if the diaper main body 8 is covered by the clothing, pants or quilt on the cared person, the light guide bar 25 can be easily wound around the clothing, pants or quilt. Moreover, since the rear end of the light guide bar 25 is easily exposed, the light beams emitted from the LED die 241 can be easily seen by the care attendant in the range of several meters. By viewing whether any optical signal (i.e., the optical signal from the LED die 241) is subjected to a change at the rear end of the light guide bar 25, the care attendant can immediately realize whether the diaper of the cared person needs to be replaced with a new one. As mentioned above, if the hip of the cared person is covered by the conventional diaper, the care attendant has to frequently examine the use condition of the diaper by performing a complicated procedure of uncovering the clothing, pants or quilt. Since the care attendant does not need to frequently uncover the diaper main body 8 to examine the use condition of the diaper, the use of the diaper of the present invention is more time-saving.

In the modern business world, parents are usually too busy to wash the contaminated diaper. Consequently, the disposable diaper gradually becomes the mainstream in the market. For complying with the requirements of the disposable diaper, the present invention provides the diaper with the excrement sensing device. As shown in FIG. 2, the diaper of the present invention comprises the detachable sensing part 1 and the electronic part 2, wherein the detachable sensing part 1 is detachably combined with the electronic part 2. The electronic part 2 comprises a first coupling part 21. The detachable sensing part 1 comprises a second coupling part 13. Due to the engagement between the first coupling part 21 and the second coupling part 13, the electronic part 2 and the detachable sensing part 1 are combined together. Consequently, the optical signal S from the emitter 201 can be introduced into the first light guide structure 11 through an input end 111 of the first light guide structure 11. After the optical signal S is sequentially transmitted through the first light guide structure 11, the light guide gap 15 and the second light guide structure 12, the optical signal S is outputted from an output end 121 of the second light guide structure 12 and received by the receiver 202. Subsequently, the warning process is implemented by the warning device 24.

When the care attendant realizes that the diaper main body 8 is contaminated by the excrement 9 according to the waning signal, the care attendant can uncover the diaper main body 8 immediately and detach the electronic part 2 from the diaper main body 8. The electronic part 2 can be reused for the next time. Since the detachable sensing part 1 is contaminated by the excrement 9, the care attendant may also detach the detachable sensing part 1 from the electronic part 2 and discard the detachable sensing part 1 along with the diaper main body 8. Then, the hip of the cared person is covered by a new diaper main body, and the detachable sensing part of the new diaper main body is combined with the electronic part 2. After the electronic part 2 is fixed on the new diaper main body through a clipping means, the electronic part 2 can be reused.

In this embodiment, the first coupling part 21 comprises a female buckle (not shown), and the second coupling part 13 comprises a male buckle (not shown). When the male buckle of the second coupling part 13 and the female buckle of the first coupling part 21 are engaged with each other, the electronic part 2 and the detachable sensing part 1 are combined together. Moreover, the detachable sensing part 1 is made of a cost-effective plastic light guide material. After the diaper is used, the detachable sensing part 1 along with the diaper main body 8 will be discarded. Consequently, the financial burden on the user is not obviously increased.

Please refer to FIG. 1 again. The electronic part 2 further comprises a clipping part 22. The user may prop open the clipping part 22 by fingers and allow the clipping part 22 to clip the diaper main body 8. Consequently, the electronic part 2 can be positioned on a specified location of the diaper main body 8 according to the user's requirements. Moreover, the detachable sensing part 1 further comprises an adhesive 14. Via the adhesive 14, the detachable sensing part 1 can be attached on the inner surface 81 of the diaper main body 8 or the inner insert layer 82, which is disposed under the inner surface 81. Preferably, the inner surface 81 of the diaper main body 8 is made of gauze.

Figure 3:
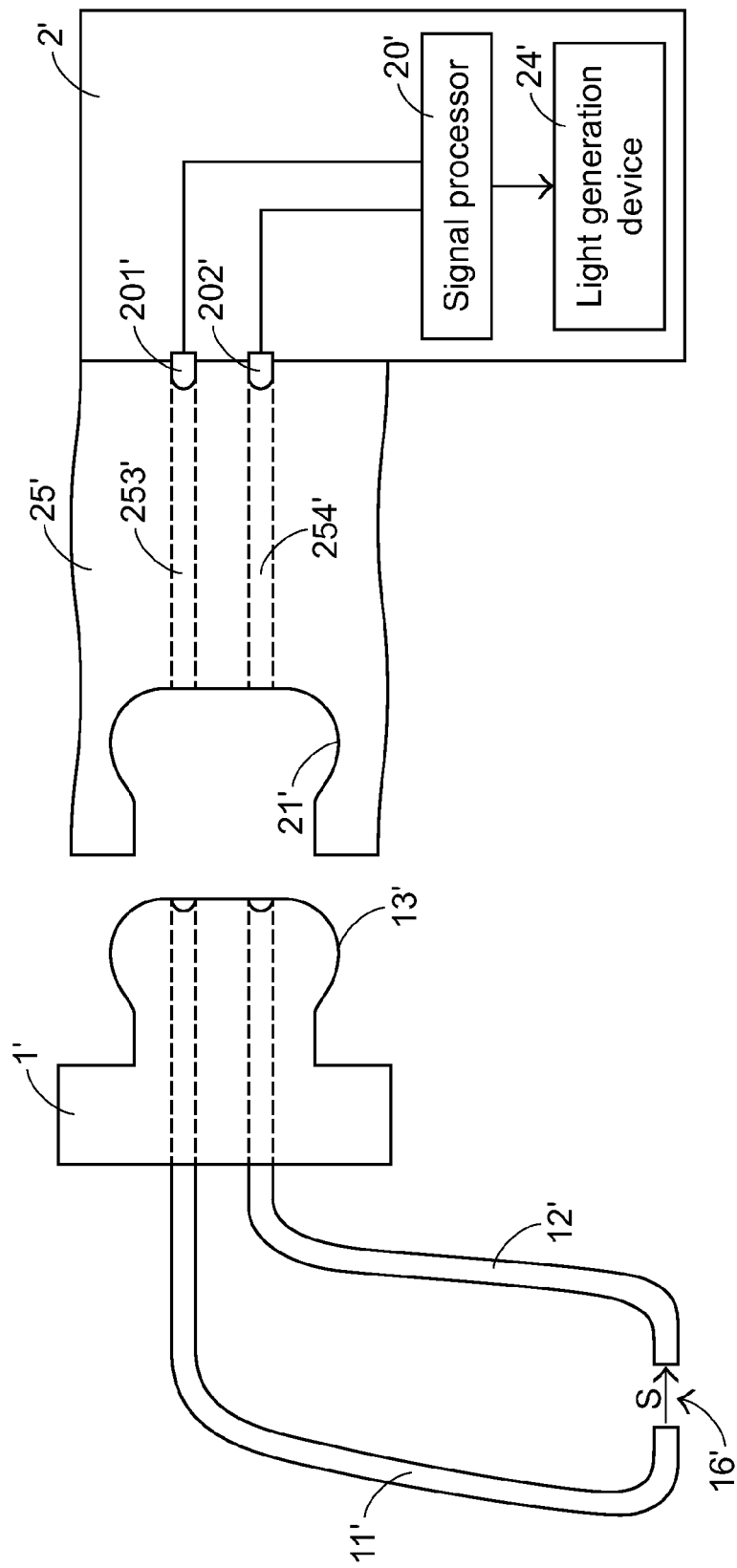
FIG. 3 schematically illustrates the relationship between an electronic part and a detachable sensing part of a diaper according to another embodiment of the present invention.

Please refer to FIG. 3. FIG. 3 schematically illustrates the relationship between an electronic part and a detachable sensing part of a diaper according to another embodiment of the present invention. In comparison with the above embodiment, the electronic part 2' of this embodiment further comprises an extension light tube structure 25'. A first end of the extension light tube structure 25' is connected with the emitter 201' and the receiver 202'. The first coupling part 21' is located at a second end of the extension light tube structure 25'. The first coupling part 21' is detachably coupled with the second coupling part 13' of the detachable sensing part 1'. The extension light tube structure 25' comprises a first light channel 253' and a second light channel 254'. When the electronic part 2' and the detachable sensing part 1' are combined together, the optical signal S from the emitter 201' is sequentially transmitted through the first light channel 253', the first light guide structure 11', the light guide gap 16', the second light guide structure 12' and the second light channel 254' and received by the receiver 202'.

Due to the arrangement of the extension light tube structure 25', the overall length of the electronic part 2' and the detachable sensing part 1' is increased. Consequently, the signal processor 20', the light generation device 24' and other precise electronic components of the electronic part 2' can be located at the positions far away from the detachable sensing part 1' (i.e., far away from the diaper main body) and placed on the clothing of the cared person. In case that the electronic part 2' is placed on the clothing of the cared person and the light generation device 24' of the electronic part 2' is exposed outside the clothing, the care attendant can easily realize the status of the light generation device 24' in a certain range.

Figure 4:
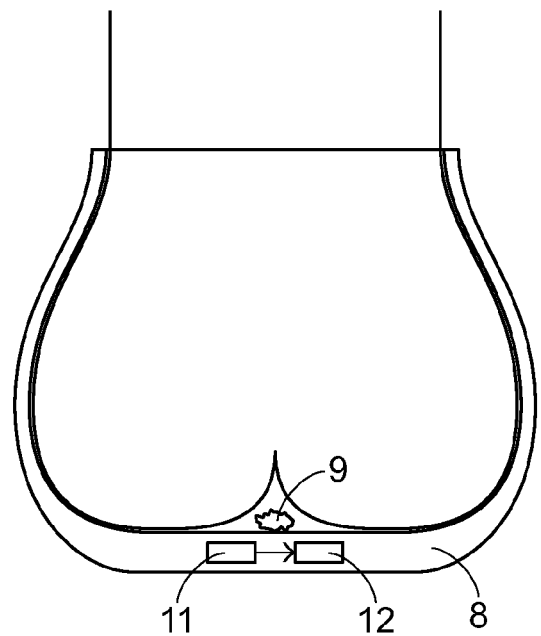
FIG. 4 is a schematic cross-sectional view illustrating a diaper with an excrement sensing device according to an embodiment of the present invention.
Figure 5:
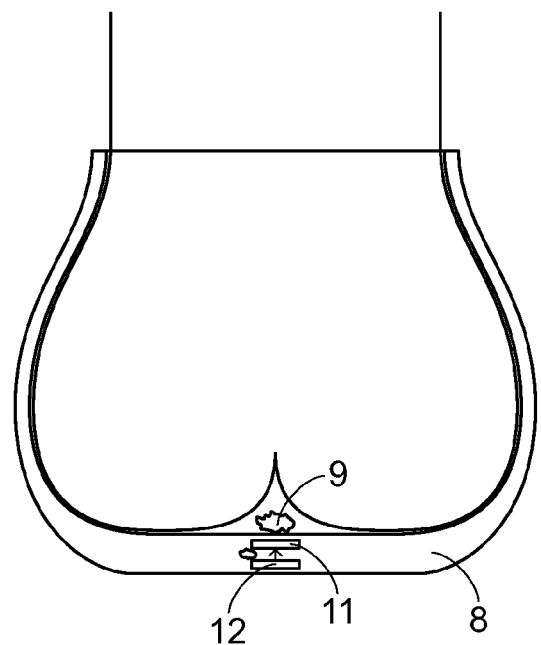
FIG. 5 is a schematic cross-sectional view illustrating a diaper with an excrement sensing device according to another embodiment of the present invention.

Please refer to FIGS. 1-5. FIG. 4 is a schematic cross-sectional view illustrating a diaper with an excrement sensing device according to an embodiment of the present invention. FIG. 5 is a schematic cross-sectional view illustrating a diaper with an excrement sensing device according to another embodiment of the present invention. As shown in FIG. 4, the hip of the cared person is covered by the diaper main body 8. Moreover, the first light guide structure 11 and the second light guide structure 12 are arranged side by side along a horizontal direction. Consequently, the excrement 9 discharged from the cared person can easily fall down to the light guide gap 15. As shown in FIG. 5, the first light guide structure 11 and the second light guide structure 12 are arranged side by side along a vertical direction. Consequently, the excrement 9 discharged from the cared person will gradually permeate into the light guide gap 15. Moreover, each of the first light guide structure 11 and the second light guide structure 12 comprises at least one light guide bar or at least one optical fiber tube.

Moreover, the detachable sensing part 1 further comprises a supporting structure 16. The supporting structure 16 is connected with and fixed on the first light guide structure 11 and the second light guide structure 12. By the supporting structure 16, the first light guide structure 11 and the second light guide structure 12 are separated from each other. Consequently, there is a specified distance between the two light guide openings 110 and 120 for allowing the excrement 9 to pass through.

As mentioned above, when the optical path of the optical signal S is disturbed by the excrement 9, the changed optical signal S is received by the warning device 24. Some examples of the detachable sensing part 1 for sensing the presence or absence of the excrement 9 will be illustrated as follows.

Figure 6:
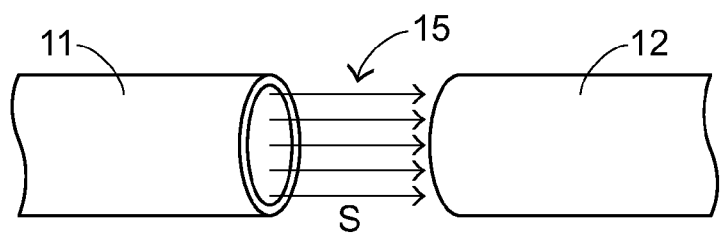
FIG. 6 is a schematic perspective view illustrating a portion of a first exemplary detachable sensing part of the excrement sensing device of the present invention, in which no excrement is sensed.
Figure 7:
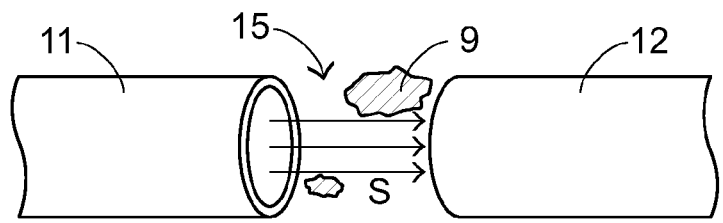
FIG. 7 is a schematic perspective view illustrating a portion of the first exemplary detachable sensing part, in which the excrement is sensed.

Please refer to FIGS. 1, 2, 6 and 7. FIG. 6 is a schematic perspective view illustrating a portion of a first exemplary detachable sensing part of the excrement sensing device of the present invention, in which no excrement is sensed. FIG. 7 is a schematic perspective view illustrating a portion of the first exemplary detachable sensing part, in which the excrement is sensed. For understanding the present invention, the light guide opening 110 of the first light guide structure 11 is located at the rear end of the in the first light guide structure 11, and the light guide opening 120 of the second light guide structure 12 is located at the rear end of the second light guide structure 12. It is noted that the light guide openings 110 and 120 are not restricted to the rear ends. For examples, in some other embodiments, the light guide openings 110 and 120 are located at lateral sides of the first light guide structure 11 and the second light guide structure 12, respectively. Preferably, the first light guide structure 11 and the second light guide structure 12 are aligned with each other, so that the optical signal S can be linearly transmitted through the first light guide structure 11 and the second light guide structure 12. As shown in FIG. 6, no excrement 9 is discharged from the cared person who is covered by the diaper main body 8. Under this circumstance, the optical path of the optical signal S from the emitter 201 is not disturbed by the excrement 9. Consequently, the optical signal S can be smoothly transmitted through the first light guide structure 11, the light guide gap 15 and the second light guide structure 12 are directly received by the receiver 202 (see FIG. 2).

As shown in FIG. 7, the excrement 9 is discharged from the cared person. The excrement 9 can easily enter the light guide gap 15. Under this circumstance, the optical path of the optical signal S from the emitter 201 is disturbed by the excrement 9. Consequently, after the optical signal S passes through the light guide gap 15, the intensity of the optical signal S is attenuated. More especially, the excrement 9 may be inhaled into the first light guide structure 11 and the second light guide structure 12 because of a siphon effect. Under this circumstance, since the first light guide structure 11 and the second light guide structure 12 are clogged, the optical path of the optical signal S is completely blocked. After the changed optical signal S is received by the receiver 202 or the optical signal S is not received by the receiver 202, the warning signal W is generated to warn the care attendant of replacing the diaper of the cared person. In other words, if the optical signal S without attenuation is smoothly transmitted to the receiver 202 through the first light guide structure 11 and the second light guide structure 12, it means that no excrement 9 is discharged to the diaper. Meanwhile, it is not necessary to take any warning action. On the other hand, if the optical signal S is subjected to the change while being transmitted through the first light guide structure 11 and the second light guide structure 12, it means that the presence of the excrement 9 in the diaper is sensed. Meanwhile, the warning action is performed.

Figure 8:
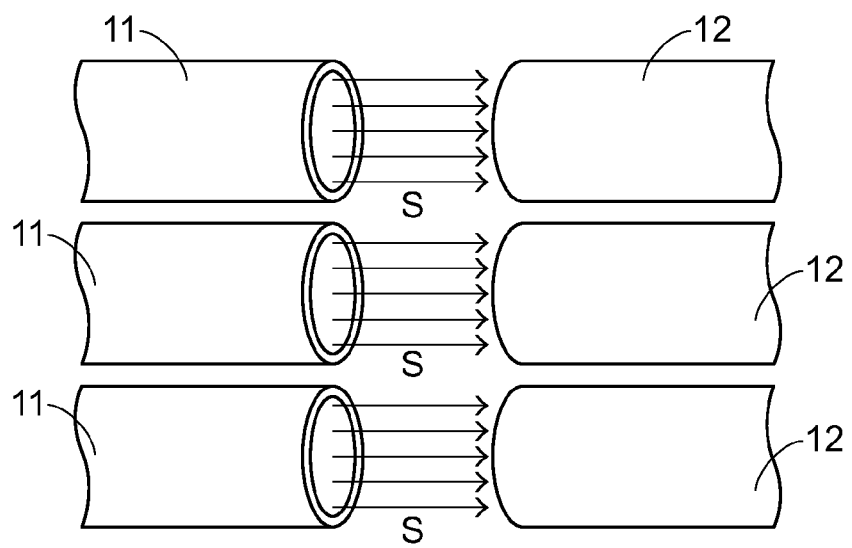
FIG. 8 is a schematic perspective view illustrating a portion of a second exemplary detachable sensing part of the excrement sensing device of the present invention.

FIG. 8 is a schematic perspective view illustrating a portion of a second exemplary detachable sensing part of the excrement sensing device of the present invention. In comparison with the first exemplary detachable sensing part, the second exemplary detachable sensing part of the excrement sensing device of the present invention comprises plural first light guide structures 11 and plural second light guide structures 12. Since the number of the optical signals S increases, the sensing accuracy will be enhanced.

Figure 9:
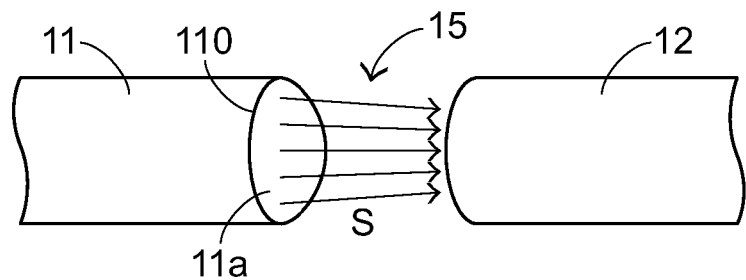
FIG. 9 is a schematic perspective view illustrating a portion of a third exemplary detachable sensing part of the excrement sensing device of the present invention.

FIG. 9 is a schematic perspective view illustrating a portion of a third exemplary detachable sensing part of the excrement sensing device of the present invention. In this embodiment, at least one of the two light guide openings 110 and 120 is equipped with a lens 11a. In this embodiment, the lens 11a is located at an inner periphery of the light guide opening 110 of the first light guide structure 11 for concentrating the optical signal S. Consequently, the optical signal S can be intensively transmitted from the first light guide structure 11 to the second light guide structure 12 through the light guide gap 15.

Figure 10:
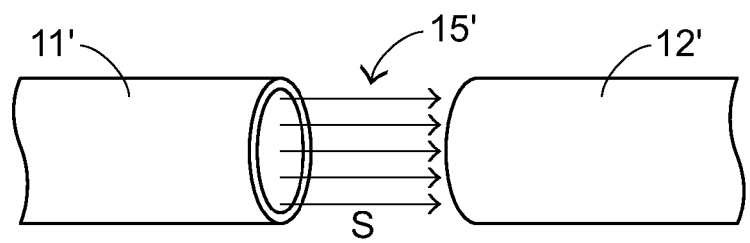
FIG. 10 is a schematic perspective view illustrating a portion of a fourth exemplary detachable sensing part of the excrement sensing device of the present invention, in which no excrement is sensed.
Figure 11:
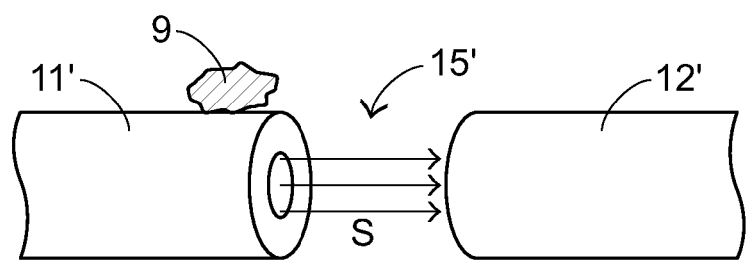
FIG. 11 is a schematic perspective view illustrating a portion of the fourth exemplary detachable sensing part, in which the excrement is sensed.

Please refer to FIGS. 1, 2, 10 and 11. FIG. 10 is a schematic perspective view illustrating a portion of a fourth exemplary detachable sensing part of the excrement sensing device of the present invention, in which no excrement is sensed. FIG. 11 is a schematic perspective view illustrating a portion of the fourth exemplary detachable sensing part, in which the excrement is sensed. In this embodiment, at least one of the rear end of the first light guide structure 11' and the rear end of the second light guide structure 12' is made of a water swelling material. When the water swelling material is in contact with the water contained in the excrement 9, the at least one rear end swells and occupies at least a portion of the light guide gap 15'. Consequently, after the optical signal S passes through the light guide gap 15', the intensity of the optical signal S is attenuated. After the changed optical signal S is received by the receiver 202, the warning signal W is generated to warn the care attendant of replacing the diaper of the cared person.

Figure 12:
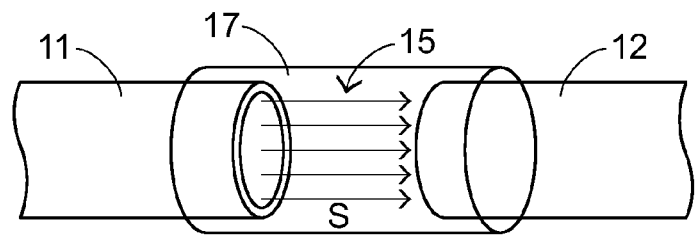
FIG. 12 is a schematic perspective view illustrating a portion of a fifth exemplary detachable sensing part of the excrement sensing device of the present invention, in which no excrement is sensed.
Figure 13:
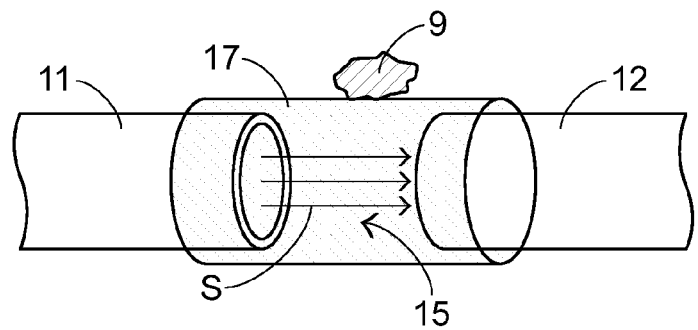
FIG. 13 is a schematic perspective view illustrating a portion of the fifth exemplary detachable sensing part, in which the excrement is sensed.

Please refer to FIGS. 1, 2, 12 and 13. FIG. 12 is a schematic perspective view illustrating a portion of a fifth exemplary detachable sensing part of the excrement sensing device of the present invention, in which no excrement is sensed. FIG. 13 is a schematic perspective view illustrating a portion of the fifth exemplary detachable sensing part, in which the excrement is sensed. In this embodiment, the detachable sensing part 1 further comprises a light guide material 17. The light guide material 17 is located at the light guide gap 15. Preferably, the light guide gap 15 is enclosed by the light guide material 17. As shown in FIG. 12, the light guide material 17 is not in contact with the water contained in the excrement 9. Under this circumstance, the light guide material 17 has high transmittance. As shown in FIG. 13, the light guide material 17 is in contact with the water contained in the excrement 9. Under this circumstance, the transmittance of the light guide material 17 is reduced. Consequently, after the optical signal S passes through the light guide gap 15, the intensity of the optical signal S is attenuated. After the changed optical signal S is received by the receiver 202, the warning signal W is generated to warn the care attendant of replacing the diaper of the cared person.

Figure 14:
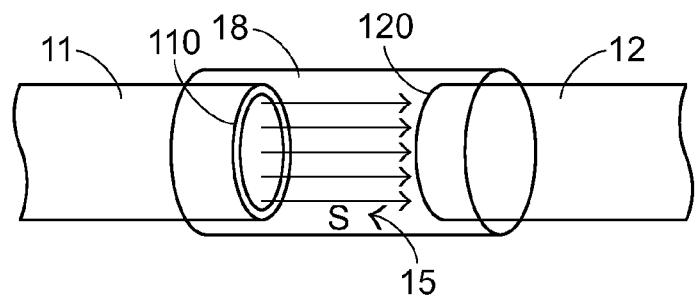
FIG. 14 is a schematic perspective view illustrating a portion of a sixth exemplary detachable sensing part of the excrement sensing device of the present invention, in which no excrement is sensed.
Figure 15:
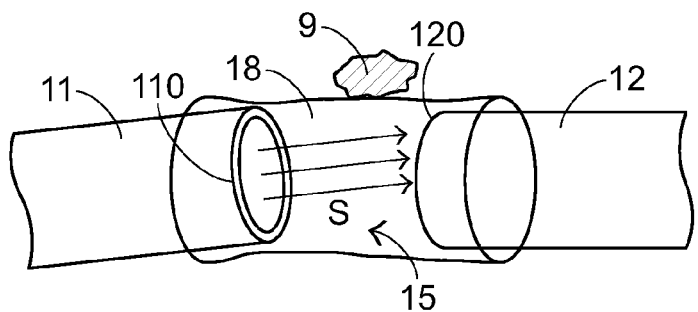
FIG. 15 is a schematic perspective view illustrating a portion of the sixth exemplary detachable sensing part, in which the excrement is sensed.

Please refer to FIGS. 1, 2, 14 and 15. FIG. 14 is a schematic perspective view illustrating a portion of a sixth exemplary detachable sensing part of the excrement sensing device of the present invention, in which no excrement is sensed. FIG. 15 is a schematic perspective view illustrating a portion of the sixth exemplary detachable sensing part, in which the excrement is sensed. In this embodiment, the detachable sensing part 1 further comprises a light guide glue 18. The light guide glue 18 is located at the light guide gap 15 for fixing the first light guide structure 11 and the second light guide structure 12, so that the two light guide openings 110 and 120 are fixedly aligned with each other. As shown in FIG. 14, the light guide glue 18 is not in contact with the water contained in the excrement 9. Under this circumstance, the two light guide openings 110 and 120 are fixed by the light guide glue 18, so that the two light guide openings 110 and 120 are aligned with each other. As shown in FIG. 15, the light guide glue 18 is in contact with the water contained in the excrement 9. Consequently, the light guide glue 18 is dissolved, cracked or disintegrated. Under this circumstance, the two light guide openings 110 and 120 are no longer fixed by the light guide glue 18, so that the two light guide openings 110 and 120 are deviated and no longer aligned with each other. Consequently, after the optical signal S passes through the light guide gap 15, the intensity of the optical signal S is attenuated. After the changed optical signal S is received by the receiver 202, the warning signal W is generated to warn the care attendant of replacing the diaper of the cared person.

Figure 16:
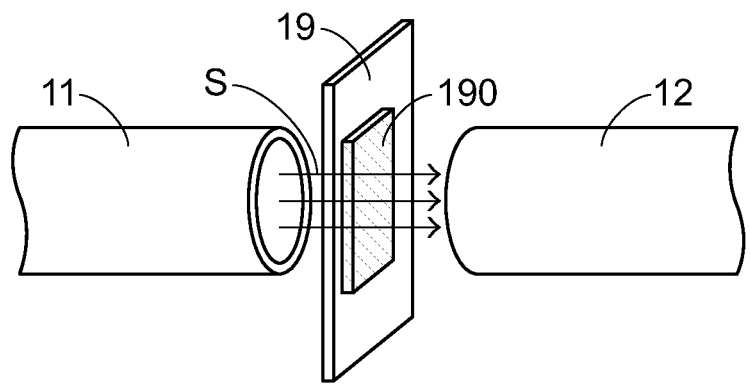
FIG. 16 is a schematic perspective view illustrating a portion of a seventh exemplary detachable sensing part of the excrement sensing device of the present invention, in which no excrement is sensed.
Figure 17:
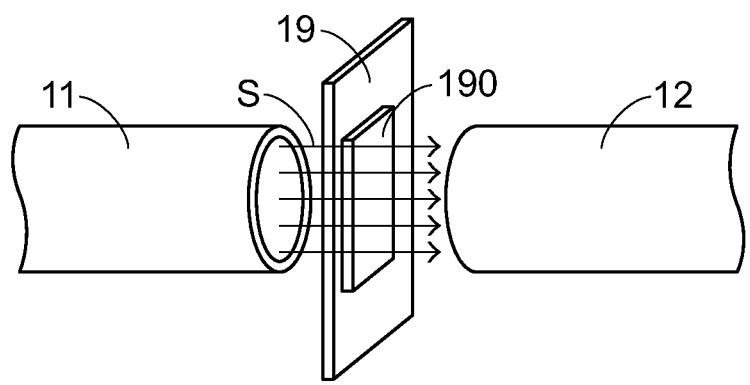
FIG. 17 is a schematic perspective view illustrating a portion of the seventh exemplary detachable sensing part, in which the excrement is sensed.

Please refer to FIGS. 1, 2, 16 and 17. FIG. 16 is a schematic perspective view illustrating a portion of a seventh exemplary detachable sensing part of the excrement sensing device of the present invention, in which no excrement is sensed. FIG. 17 is a schematic perspective view illustrating a portion of the seventh exemplary detachable sensing part, in which the excrement is sensed. In this embodiment, the detachable sensing part further comprises a detection test strip 19. The detection test strip 19 is arranged between the rear end of the first light guide structure 11 and the rear end of the second light guide structure 12. That is, the detection test strip 19 is disposed in the optical path of the optical signal S. When the detection test strip 19 is in contact with the excrement 9, the color of the detection test strip 19 is subjected to a change because the pH value or the water content is changed. The detection test strip 19 with the changed color may disturb the optical path of the optical signal S. After the changed optical signal S is received by the receiver 202, the warning signal W is generated to warn the care attendant of replacing the diaper of the cared person. For example, the detection test strip 19 is a thin film printed with color-variable ink 190. In an example, when the color-variable ink 190 is in contact with the excrement 9, the color of the color-variable ink 190 is switched from a deep color to a light color. Consequently, after the optical signal S passes through the light color ink, the intensity of the optical signal S is strengthened. After the changed optical signal S is received by the receiver 202, the warning signal W is generated to warn the care attendant of replacing the diaper of the cared person. In a variant example, when the color-variable ink is in contact with the excrement 9, the color of the color-variable ink 190 is switched from a light color to a deep color. Consequently, after the optical signal S passes through the light color ink, the intensity of the optical signal S is attenuated. After the changed optical signal S is received by the receiver 202, the warning signal W is generated to warn the care attendant of replacing the diaper of the cared person.

From the above descriptions, the present invention provides a diaper with an excrement sensing device. The excrement sensing device comprises a detachable sensing part and an electronic part. The detachable sensing part and the electronic part are detachably combined with each other. The electronic part comprises a signal processor with higher cost. The electronic part may be located at any position of the diaper main body with the proviso that the electronic part is not easily contaminated by the excrement. Moreover, the electronic part can be reused. Moreover, the detachable sensing part has lower cost and is discarded along with the diaper main body. The excrement sensing device of the present invention senses the excrement according to the optical signal in replace of the electrical signal. Consequently, the diaper user will not have the psychological fear of the possible electric shock. Moreover, when the excrement is discharged from the cared person, the excrement sensing device of the diaper of the present invention can immediately sense the excrement and actively notify the care attendant that it is time to replace the diaper of the cared person with a new one. By using the diaper of the present invention, the contact time of the excrement with the skin of the cared person will be largely reduced. Consequently, the use of the diaper of the present invention can effectively prevent urinary tract infection, diaper rash and other diseases. In other words, the diaper of the present invention is more user-friendly.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:
1. A diaper with an excrement sensing device, the diaper comprising:
   a detachable sensing part comprising a first light guide structure and a second light guide structure, wherein the first light guide structure has a first light guide opening, the second light guide structure has and a second light guide opening, and a light guide gap is formed between the first light guide opening and the second light guide opening;
   an electronic part comprising a signal processor, an emitter and a receiver, wherein the detachable sensing part is detachably combined with the electronic part, and an optical signal is emitted by the emitter, wherein after the optical signal is transmitted through the first light guide structure, the light guide gap and the second light guide structure, the optical signal is received by the receiver; and a diaper main body, wherein the detachable sensing part is disposed within the diaper main body, wherein when an excrement enters the light guide gap or contacts with the detachable sensing part, the optical signal is subjected to a change, wherein in response to the change of the optical signal, the signal processor generates a warning signal;

wherein, the electronic part comprises an extension light tube structure and a first coupling part, and the detachable sensing part comprises a second coupling part matching the first coupling part, the first coupling part is located at an end of the extension light tube structure, and the first coupling part is engageable with the second coupling part of the detachable sensing part, wherein the extension light tube structure comprises a first light channel and a second light channel, wherein when the electronic part and the detachable sensing part are combined together, the optical signal from the emitter is sequentially transmitted through the first light channel, the first light guide structure, the light guide gap, the second light guide structure and the second light channel and received by the receiver; or wherein, the electronic part further comprises a clipping part that clips the diaper main body or the clothing of the diaper user, wherein when the diaper main body is clipped by the clipping part, the electronic part is positioned on a specified location of the diaper main body, wherein when the clothing of the diaper user is clipped by the clipping part, a light generation device of the electronic part is exposed outside the clothing; or wherein, the detachable sensing part further comprises an adhesive, the diaper main body further comprises an inner surface and an inner insert layer under the inner surface, and the inner surface of the diaper main body is made of gauze, wherein the detachable sensing part is attached on the inner surface or the inner insert layer of the diaper main body via the adhesive, or the detachable sensing part is fixedly installed on the inner surface of the diaper main body; or wherein the first light guide opening of the first light guide structure is located at a rear end of the first light guide structure, and the second light guide opening of the second light guide structure is located at a rear end of the second light guide structure, wherein the first light guide opening and the second light guide opening correspond to each other.

2. The diaper according to claim 1, wherein the electronic part further comprises a warning device, and the warning device is in communication with the signal processor to receive the warning signal, wherein if the warning device is the light generation device, the light generation device generates a warning light after the warning signal is sent to the light generation device, wherein if the warning device is a sound generation device, the sound generation device generates a warning sound after the warning signal is sent to the sound generation device, wherein if the warning device is a wireless transmitter, the wireless transmitter issues a wireless warning signal to an external electronic device after the warning signal is sent to the wireless transmitter, wherein if the warning device comprises a light generation device and a light guide bar and the light guide bar is connected with the light generation device, plural light beams emitted by the light generation device are introduced into a front end of the light guide bar and outputted from a rear end of the light guide bar after the warning signal is received by the warning device, and the rear end of the light guide bar is exposed outside a clothing of a diaper user.

3. The diaper according to claim 2, wherein when the first coupling part and the second coupling part are engaged with each other, the electronic part and the detachable sensing part are combined together, so that the optical signal from the emitter is introduced into the first light guide structure through an input end of the first light guide structure, wherein after the optical signal is sequentially transmitted through the first light guide structure, the light guide gap and the second light guide structure, the optical signal is outputted from an output end of the second light guide structure and received by the receiver.

4. The diaper according to claim 2, wherein the first light guide opening and the second light guide opening are aligned with each other, or at least one of the first light guide opening and the second light guide opening is equipped with a lens to concentrate the optical signal, so that the concentrated optical signal is transmitted from the first light guide structure to the second light guide structure through the light guide gap; or wherein at least one of the rear end of the first light guide structure and the rear end of the second light guide structure is made of a water swelling material, wherein when the water swelling material is in contact with the excrement, the rear end formed of the water swelling material swells and occupies at least a portion of the light guide gap, so that an intensity of the optical signal passing through the light guide gap is attenuated, wherein after the changed optical signal is received by the receiver, the warning signal is generated; or wherein the detachable sensing part further comprises a detection test strip, and the detection test strip is arranged between the rear end of the first light guide structure and the rear end of the second light guide structure, wherein when the detection test strip is in contact with the excrement, a color of the detection test strip is changed, wherein after the changed optical signal is received by the receiver, the warning signal is generated.

5. The diaper according to claim 4, wherein the detection test strip is a thin film printed with color-variable ink, wherein when the color-variable ink is in contact with the excrement, a color of the color-variable ink becomes deeper, so that an intensity of the optical signal received by the receiver is attenuated; or when the color-variable ink is in contact with the excrement, the color of the color-variable ink becomes lighter, so that an intensity of the optical signal received by the receiver is strengthened.

6. The diaper according to claim 2, wherein the detachable sensing part further comprises a light guide material, and the light guide material is located at the light guide gap, wherein when the light guide material is not in contact with water, the light guide material has high transmittance, wherein when the light guide material is in contact with water, the transmittance of the light guide material is reduced, so that an intensity of the optical signal passing through the light guide gap is attenuated, wherein after the changed optical signal is received by the receiver, the warning signal is generated; or wherein the detachable sensing part further comprises a light guide glue, and the light guide glue is located at the light guide gap, wherein when the light guide glue is not in contact with water, the first light guide opening and the second light guide opening are fixed by the light guide glue, so that the first light guide opening and the second light guide opening are aligned with each other, wherein when the light guide glue is in contact with water, the light guide glue is dissolved, cracked or disintegrated, so that the first light guide opening and the second light guide opening are no longer aligned with each other and an intensity of the optical signal passing through the light guide gap is attenuated, wherein after the changed optical signal is received by the receiver, the warning signal is generated.

7. The diaper according to claim 1, wherein the detachable sensing part further comprises at least one supporting structure, and the at least one supporting structure is connected with the first light guide structure and the second light guide structure, wherein the first light guide structure and the second light guide structure are separated from each other by the supporting structure, so that there is a specified distance between the first light guide opening and the second light guide opening; or wherein each of the first light guide structure and the second light guide structure comprises at least one light guide bar or at least one optical fiber tube, wherein the first light guide structure and the second light guide structure are arranged side by side along a horizontal direction, or the first light guide structure and the second light guide structure are arranged side by side along a vertical direction; or wherein the first light guide structure and the second light guide structure are arranged side by side, the first light guide opening and the second light guide opening are aligned with each other, the first light guide opening and the second light guide opening are located at first ends of the first light guide structure and the second light guide structure, and the electronic part is located at second ends of the first light guide structure and the second light guide structure.

8. An excrement sensing device for a diaper, the excrement sensing device comprising:
a detachable sensing part comprising a first light guide structure and a second light guide structure, wherein the first light guide structure has a first light guide opening, the second light guide structure has a second light guide opening, and a light guide gap is formed between the first light guide opening and the second light guide opening; and
an electronic part comprising a signal processor, an emitter and a receiver, wherein the detachable sensing part is detachably combined with the electronic part, and an optical signal is emitted by the emitter, wherein after the optical signal is transmitted through the first light guide structure, the light guide gap and the second light guide structure, the optical signal is received by the receiver,
wherein the detachable sensing part and the electronic part are detachably disposed on a diaper main body, wherein when an excrement enters the light guide gap or contacts with the detachable sensing part, the optical signal is subjected to a change, wherein in response to the change of the optical signal, the signal processor generates a warning signal;
wherein the electronic part comprises an extension light tube structure and a first coupling part, and the detachable sensing part comprises a second coupling part matching the first coupling part, the first coupling part is located at an end of the extension light tube structure, and the first coupling part is engageable with the second coupling part of the detachable sensing part, wherein the extension light tube structure comprises a first light channel and a second light channel, wherein when the electronic part and the detachable sensing part are combined together, the optical signal from the emitter is sequentially transmitted through the first light channel, the first light guide structure, the light guide gap, the second light guide structure and the second light channel and received by the receiver; or
wherein the electronic part further comprises a clipping part that clips the diaper main body or the clothing of the diaper user, wherein when the diaper main body is clipped by the clipping part, the electronic part is positioned on a specified location of the diaper main body, wherein when the clothing of the diaper user is clipped by the clipping part, a light generation device of the electronic part is exposed outside the clothing; or
wherein the detachable sensing part further comprises an adhesive, the diaper main body further comprises an inner surface and an inner insert layer under the inner surface, and the inner surface of the diaper main body is made of gauze, wherein the detachable sensing part is attached on the inner surface or the inner insert layer of the diaper main body via the adhesive, or the detachable sensing part is fixedly installed on the inner surface of the diaper main body; or wherein the first light guide opening of the first light guide structure is located at a rear end of the first light guide structure, and the second light guide opening of the second light guide structure is located at a rear end of the second light guide structure, wherein the first light guide opening and the second light guide opening correspond to each other.

9. The excrement sensing device according to claim 8, wherein the electronic part further comprises a warning device, and the warning device is in communication with the signal processor to receive the warning signal, wherein if the warning device is the light generation device, the light generation device generates a warning light after the warning signal is sent to the light generation device, wherein if the warning device is a sound generation device, the sound generation device generates a warning sound after the warning signal is sent to the sound generation device, wherein if the warning device is a wireless transmitter, the wireless transmitter issues a wireless warning signal to an external electronic device after the warning signal is sent to the wireless transmitter, wherein if the warning device comprises a light generation device and a light guide bar and the light guide bar is connected with the light generation device, plural light beams emitted by the light generation device are introduced into a front end of the light guide bar and outputted from a rear end of the light guide bar after the warning signal is received by the warning device, and the rear end of the light guide bar is exposed outside a clothing of a diaper user.

10. The excrement sensing device according to claim 9, wherein when the first coupling part and the second coupling part are engaged with each other, the electronic part and the detachable sensing part are combined together, so that the optical signal from the emitter is introduced into the first light guide structure through an input end of the first light guide structure, wherein after the optical signal is sequentially transmitted through the first light guide structure, the light guide gap and the second light guide structure, the optical signal is outputted from an output end of the second light guide structure and received by the receiver.

11. The excrement sensing device according to claim 9, wherein the first light guide opening and the second light guide opening are aligned with each other, or at least one of the first light guide opening and the second light guide opening is equipped with a lens to concentrate the optical signal, so that the concentrated optical signal is transmitted from the first light guide structure to the second light guide structure through the light guide gap; or wherein at least one of the rear end of the first light guide structure and the rear end of the second light guide structure is made of a water swelling material, wherein when the water swelling material is in contact with the excrement, the rear end formed of the water swelling material swells and occupies at least a portion of the light guide gap, so an intensity of the optical signal passing through the light guide gap is attenuated, wherein after the changed optical signal is received by the receiver, the warning signal is generated; or wherein the detachable sensing part further comprises a detection test strip, and the detection test strip is arranged between the rear end of the first light guide structure and the rear end of the second light guide structure, wherein when the detection test strip is in contact with the excrement, a color of the detection test strip is changed, wherein after the changed optical signal is received by the receiver, the warning signal is generated.

12. The excrement sensing device according to claim 11, wherein the detection test strip is a thin film printed with color-variable ink, wherein when the color-variable ink is in contact with the excrement, a color of the color-variable ink becomes deeper, so that an intensity of the optical signal received by the receiver is attenuated; or when the color-variable ink is in contact with the excrement, the color of the color-variable ink becomes lighter, so that an intensity of the optical signal received by the receiver is strengthened.

13. The excrement sensing device according to claim 9, wherein the detachable sensing part further comprises a light guide material, and the light guide material is located at the light guide gap, wherein when the light guide material is not in contact with water, the light guide material has high transmittance, wherein when the light guide material is in contact with water, the transmittance of the light guide material is reduced, so that an intensity of the optical signal passing through the light guide gap is attenuated, wherein after the changed optical signal is received by the receiver, the warning signal is generated; or wherein the detachable sensing part further comprises a light guide glue, and the light guide glue is located at the light guide gap, wherein when the light guide glue is not in contact with water, the first light guide opening and the second light guide opening are fixed by the light guide glue, so that the first light guide opening and the second light guide opening are aligned with each other, wherein when the light guide glue is in contact with water, the light guide glue is dissolved, cracked or disintegrated, so that the first light guide opening and the second light guide opening are no longer aligned with each other and an intensity of the optical signal passing through the light guide gap is attenuated, wherein after the changed optical signal is received by the receiver, the warning signal is generated.

14. The excrement sensing device according to claim 8, wherein the detachable sensing part further comprises at least one supporting structure, and the at least one supporting structure is connected with the first light guide structure and the second light guide structure, wherein the first light guide structure and the second light guide structure are separated from each other by the supporting structure, so that there is a specified distance between the first light guide opening and the second light guide opening; or wherein each of the first light guide structure and the second light guide structure comprises at least one light guide bar or at least one optical fiber tube, wherein the first light guide structure and the second light guide structure are arranged side by side along a horizontal direction, or the first light guide structure and the second light guide structure are arranged side by side along a vertical direction; or wherein the first light guide structure and the second light guide structure are arranged side by side, the first light guide opening and the second light guide opening are aligned with each other, the first light guide opening and the second light guide opening are located at first ends of the first light guide structure and the second light guide structure, and the electronic part is located at second ends of the first light guide structure and the second light guide structure.

\* \* \* \* \*